Aug. 12, 1941. W. I. JOHNSTON Plant Pat. 483
ROSE PLANT
Filed March 26, 1941
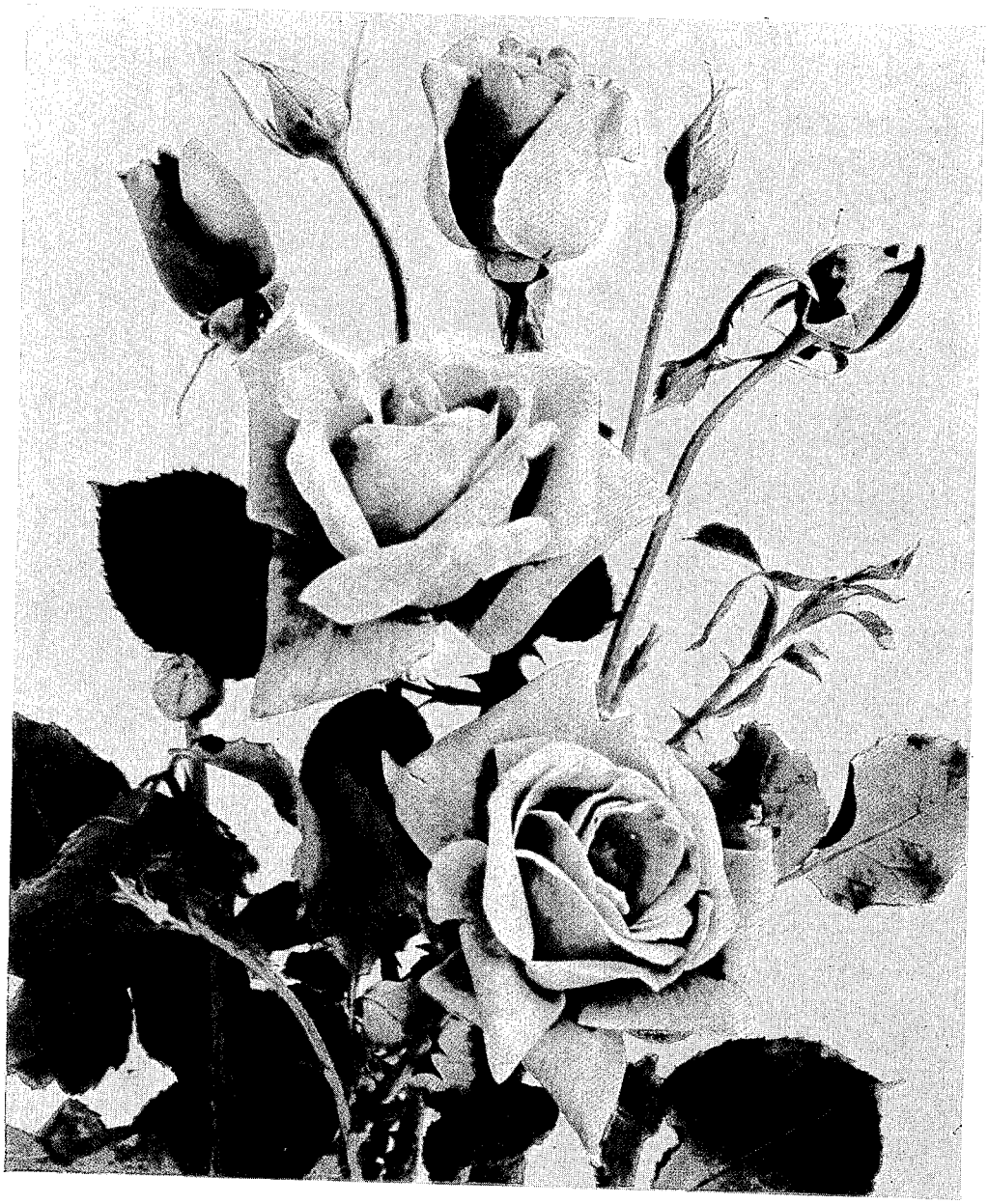
Inventor
W. I. Johnston
By Robb & Robb
Attorneys Patented Aug. 12, 1941

UNITED STATES PATENT OFFICE

483

ROSE PLANT

Walter Irwin Johnston, Portadown, Northern Ireland, assignor to Jackson & Perkins Company, Newark, N. Y.

Application March 26, 1941, Serial No. 385,373

1 Claim. (Cl. 47—61)

The present invention relates to improvements in hybrid tea rose plants, and in particular to a new and distinct variety of this class produced by crossing "Sir David Davis" and "Southport."

The origination herein disclosed in detail presents a number of distinctions, unusual in character, and important in a rose of this type both botanically and commercially. Among these distinctions, the following are deemed to be primary:

(1) The color of the buds, Pomegranate Purple, changing to Tyrian Red to Rose Red in the half open stage of development of the flower;

(2) The extra large sized flowers; the peculiar formation of one sepal which protrudes almost like a miniature leaf;

(3) The protrusion of the ovaries, causing the seeds to form outside of the seed pod; the Sanford's Brown veining in the Light Green on the under side of the leaf;

(4) And tall narrow upright growth of the plant.

The illustration depicts as closely as possible the characteristics of the rose in the various stages of development.

The following is a detail description of the new variety, color terminology according with Ridgway's Color Standard.

Parentage: Seedling.

*Seed parent.*—Sir David Davis.

*Pollen parent.*—Southport.

Classification: Botanic and commercial—hybrid tea.

*Flower*

(Observations made in the morning of October 1, 1940, at Newark, New York.)

Blooming habit: Recurrent—continuous.

Bud:

*Size.*—Large.

*Form.*—Long, pointed. Is not affected by wet or hot weather.

*Color.*—When sepals first divide—Pomegranate Purple, Plate 12. When petals begin to unfurl—Carmine, Plate 1. When half blown: inside of petals—between Tyrian Rose, Plate 12, and Rose Red, Plate 12; reverse of petals—Tyrian Rose, Plate 12, lightening to Rose Color, Plate 12.

*Sepals.*—Serrated, branched, one sepal on each flower usually very long and prominent. Curl back when petals unfurl. *Color*: outside—Biscay Green, Plate 17. Inside—Courge Green, Plate 17. Large sepal, almost a miniature leaf-serration on edges of large sepal, Morocco Red, Plate 1.

*Calyx.*—*Shape*—funnel. *Size*—small. *Aspect*—smooth. *Odor when rubbed*—none. *Color*—Biscay Green, Plate 17.

*Peduncle.*—*Length*—long. *Aspect*—rough. *Color*—Citrine, Plate 4, overlaid with Amber Brown, Plate 3. *Strength*—stiff; heavy.

*Opening.*—Bud opens well. Is not affected by adverse conditions.

Bloom:

*Size.*—Large. Average size when fully expanded—5½ inches.

*Borne.*—Several together.

*Stems.*—Long; strong.

*Form.*—When first open—cupped. Permanence—retains its form to the end.

*Petalage.*—Double (full but open center). Number of petals under normal conditions—22.

*Color.*—Center of flower—between Tyrian Rose, Plate 12, and Rose Red, Plate 12. Outer petals—Tyrian Rose, Plate 12. Base of petals (aiglet)—Empire Yellow, Plate 4. Inside of petals—Tyrian Rose, Plate 12. Reverse of petals—between Tyrian Rose, Plate 12, and Rose Color, Plate 12. General tonality from a distance—Tyrian Rose, Plate 12.

*Discoloration.*—General tonality at end of first day—Tyrian Rose, Plate 12. Second day—Rose Red, Plate 12. Third day—Between Rose Red, Plate 12, and Rose Color, Plate 12.

Petals:

*Texture.*—Thick. Is not affected by wet or hot weather.

*Appearance.*—Outside—shiny. Inside—velvety.

*Form.*—Oval, notched.

*Arrangement.*—Informal (with "rags" in center). Petaloids in center—few; small.

*Persistence.*—Drop off cleanly.

*Fragrance.*—Strong. *Nature.*—Sweet Briar.

*Lasting quality.*—On the plant and as cut flower—long.

Genital organs:

*Stamens, anthers.*—Large, many. *Color*—Primuline Yellow, Plate 16. *Arrangement*—regular around styles.

*Stamens, filaments (threads).*—Long. *Color*—Eugenia Red, Plate 13.

*Pollen.*—Mustard Yellow, Plate 16.

*Styles.*—Bunched, uneven length; medium length; thin.

*Stigmas.*—Amber Yellow, Plate 16.
*Ovaries.*—All protruding from calyx.

*Plant*

Form: Bush.
Growth: Vigorous; upright.
Foliage: 5-7 leaflets.
*Size.*—Large.
*Quantity.*—Normal.
*Color.*—*New foliage:* upper side—Garnet Brown, Plate 1; under side—Oxblood Red. *Old foliage:* upper side—Dark Cress Green, Plate 31; under side—Light Cress Green, Plate 31, with veining of Sanford's Brown, Plate 2.
*Shape.*—Oval pointed.
*Texture.*—Upper side—leathery, glossy. Under side—rough. *Ribs and veins*—prominent.
*Edge.*—Serrated (saw toothed).
*Serration.*—Single; small; sharp.
*Rachis.*—Upper side—Hay's Russet, Plate 14. Under side—Dull Citrine, Plate 16; smooth.
*Stipules.*—Long; slightly bearded.
*Disease resistance.*—Resistant.

Wood:
*New wood.*—*Color*—Acajou Red, Plate 13. *Bark*—smooth.
*Old wood.*—*Color*—Cress Green, Plate 31. *Bark*—smooth.

Thorns (thorns are divided into thorns, prickles, and short needles):
*Thorns.*—On main stalks from base and on laterals from stalk—many. *Form*—broad base; medium length; hooked downward. *Color when young*—Van Dyke Red, Plate 13. *Position*—irregular.
*Prickles.*—On main stalks and on laterals—many. *Color*—Acajou Red, Plate 13.

I claim:

A new and distinct variety of hybrid tea rose plant, characterized as to novelty by its tall, narrow, upright habit of growth, the color of the veins in contrast with the background of the under side of the leaves, the protruding ovaries and peculiar formation of one of the sepals, in combination with the color and size of the flowers in their different stages of development, substantially as shown and described.

WALTER IRWIN JOHNSTON.